United States Patent
Spahr et al.

(10) Patent No.: US 11,312,932 B2
(45) Date of Patent: Apr. 26, 2022

(54) METHOD AND DEVICE FOR PRODUCING BIOGAS

(71) Applicant: Herbst Umwelttechnik GmbH, Berlin (DE)

(72) Inventors: Marcel Spahr, Berlin (DE); Leonhard Fechter, Berlin (DE)

(73) Assignee: Herbst Umwelttechnik GmbH, Berlin (DE)

( * ) Notice: Subject to any disclaimer, the term of this patent is extended or adjusted under 35 U.S.C. 154(b) by 248 days.

(21) Appl. No.: 16/481,702

(22) PCT Filed: Jan. 29, 2018

(86) PCT No.: PCT/EP2018/052180
§ 371 (c)(1),
(2) Date: Jul. 29, 2019

(87) PCT Pub. No.: WO2018/138368
PCT Pub. Date: Aug. 2, 2018

(65) Prior Publication Data
US 2019/0382700 A1    Dec. 19, 2019

(30) Foreign Application Priority Data
Jan. 30, 2017   (EP) ..................................... 17153818

(51) Int. Cl.
*C12M 1/107* (2006.01)
*C12M 1/00* (2006.01)
(Continued)

(52) U.S. Cl.
CPC ............ *C12M 21/04* (2013.01); *C12M 23/58* (2013.01); *C12M 29/18* (2013.01); *C12M 45/02* (2013.01);
(Continued)

(58) Field of Classification Search
CPC ...................................................... C12M 21/04
See application file for complete search history.

(56) References Cited

U.S. PATENT DOCUMENTS 5,500,123 A * 3/1996 Srivastava ................ C02F 3/28
                                                                 210/603
6,296,766 B1 * 10/2001 Breckenridge ........ C12M 23/36
                                                                 210/613
(Continued)

FOREIGN PATENT DOCUMENTS

DE    19532359 A1    3/1997
DE    20121701       3/2003
(Continued)

OTHER PUBLICATIONS

Maus et al., "Unraveling the microbiome of a thermophilic biogas plant by metagenome and metatranscriptome analysis complemented by characterization of bacterial and archaeal isolates" Biotechnol Biofuels, Aug. 11, 2016;9:171 (Year: 2016).*

(Continued)

*Primary Examiner* — Jonathan M Hurst
(74) *Attorney, Agent, or Firm* — Schwegman Lundberg & Woessner, P.A.

(57) ABSTRACT

The invention relates to a method and a biogas plant for producing biogas, preferably from rice straw, wherein a substrate is fermented in two reactors (1, 2) in a circulating manner, so that a methane production from cellulose-and/or lignocellulose-containing substrate can be improved.

16 Claims, 5 Drawing Sheets

Figure 1A:
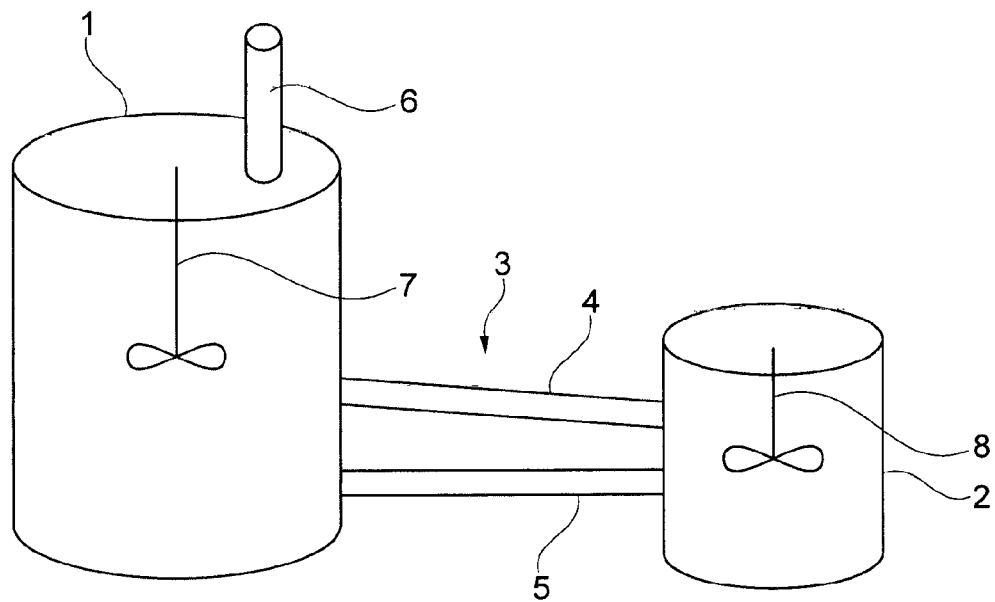

(51) Int. Cl.
*C12M 1/33* (2006.01)
*C12P 5/02* (2006.01)

(52) U.S. Cl.
CPC .............. *C12M 45/20* (2013.01); *C12P 5/023* (2013.01); *C12P 2203/00* (2013.01)

(56) References Cited

U.S. PATENT DOCUMENTS

| | | | |
|---|---|---|---|
| 6,299,774 B1 * | 10/2001 | Ainsworth | C12M 21/04 210/603 |
| 7,560,026 B2 * | 7/2009 | Wilson | C02F 3/286 210/179 |
| 2003/0085171 A1 * | 5/2003 | Khudenko | C12M 21/04 210/603 |
| 2009/0035832 A1 * | 2/2009 | Koshland, Jr. | C12M 23/36 435/167 |
| 2010/0093046 A1 * | 4/2010 | Remmereit | C12M 41/18 435/134 |
| 2011/0091954 A1 * | 4/2011 | Chen | C12M 29/02 435/168 |
| 2013/0309759 A1 * | 11/2013 | Kennedy | B01D 53/62 435/266 |
| 2016/0185632 A1 * | 6/2016 | Lesty | C12M 29/24 210/603 |
| 2019/0203250 A1 * | 7/2019 | Hansen | C12M 45/09 |

FOREIGN PATENT DOCUMENTS

| | | |
|---|---|---|
| DE | 102006008026 A1 | 8/2007 |
| DE | 102013114786 A1 | 6/2015 |
| EP | 2679688 A1 | 1/2014 |
| EP | 2927308 A1 | 10/2015 |
| WO | WO-0206439 A2 | 1/2002 |
| WO | WO-2004016797 A1 | 2/2004 |
| WO | WO-2006048008 A2 | 5/2006 |

OTHER PUBLICATIONS

"International Application Serial No. PCT/EP2018/052180, International Search Report dated Apr. 17, 2018", w/ English Translation, (dated Apr. 17, 2018), 9 pgs.

"International Application Serial No. PCT/EP2018/052180, Written Opinion dated Apr. 17, 2018", (dated Apr. 17, 2018), 9 pgs.

* cited by examiner

METHOD AND DEVICE FOR PRODUCING BIOGAS

PRIORITY APPLICATIONS

This application is a U.S. National Stage Filing under 35 U.S.C. 371 from International Application No. PCT/EP2018/052180, filed on Jan. 29, 2018, and published as WO2018/138368 on Aug. 2, 2018, which claims the benefit of priority to European Application No. 17153818.4, filed on Jan. 30, 2017; the benefit of priority of each of which is hereby claimed herein, and which applications and publication are hereby incorporated herein by reference in their entireties.

The invention relates to a method and to a device for producing biogas.

Biogas is produced in biogas facilities which are used for example in agriculture and are mostly fed with animal excrement or energy crops as a substrate. The biogas occurs as a metabolic product of bacteria and microorganisms on fermentation of the organic material. Biogas is a gas mixture of methane ($CH_4$) and carbon dioxide ($CO_2$), with up to 2% hydrogen sulphide ($H_2S$) and trace gases such as ammonia ($NH_3$), hydrogen ($H_2$), nitrogen ($N_2$) and carbon monoxide (CO).

Biogas can be produced from almost all organic substances with the basic constituents of fat, protein, and carbohydrates. Straw (wheat straw, rapeseed straw, amongst others) which above all contains cellulose and lignocellulose is very difficult to be broken down in an anaerobic process and for this reason is used to a lesser extent or is subjected to a pre-treatment. It is particularly rice straw which due to the high lignin and silicate shares is difficult to break down compared to easily fermentable raw materials such as maize silage and therefore achieves lower biogas yields in conventional biogas facilities.

EP 2 927 308 A1 relates to a method and a biogas facility for producing biogas from straw. Herein, means for pre-treating the straw are provided in order to effect a mechanical breakdown thereof before the straw is brought into a fermenter, in which an anaerobic, bacterial fermentation takes place. The pre-treatment of the straw by way of grinding in a hammer mill, as is suggested for example in EP 2 927 308 A1, is costly and leads to a sticking of the fermentation mass, so that a percolation and hence a biogas formation are hampered.

It is therefore the object of the invention to suggest an improved method for the production of biogas. In particular, the invention can be based on the object of improving a method with regard to its economic efficiency. Furthermore, the invention can also be based on suggesting a method which improves a biogas production from straw and/or permits a biogas production from rice straw. The invention can moreover have the object of suggesting a biogas facility for carrying out the method.

The object is achieved by a method according to claim 1 as well as by a biogas facility with the features of the further independent claim. Advantageous embodiments result from the features of the dependent claims and the embodiment examples.

The suggested method for producing biogas herein comprises the following steps. The described steps do not need to be carried out in the specified sequence.

A cellulose-containing and/or lignocellulose-containing substrate, such as straw or rice straw, is at least partly fermented with mesophilic bacteria in a first reactor during a first residence time. Herein, the temperature in the reactor is at least 20° C., preferably at least 25° C., particularly preferably at least 30° C. and/or at the most 55° C., preferably at the most 43° C., particularly preferably at the most 46° C. The temperature can be adjusted by way of heating the contents of the first reactor and/or can set in at least partly by way of exothermic reactions of the bacterial metabolic processes on methane production. The mesophilic bacteria are suitable for producing methane from acetic acid. It should be noted that "bacteria" here is to be understood in the broadest context. It is scientifically disputed whether archaea and bacteria are different taxa. Here however, in particular archaea are also to be understood as bacteria. Herein, the archaea can preferably be of the order of Methanobacteriales, Methanococcales, Methanomicrobiales, Methanocellales, Methanosarcinales, Methanoscarcina, Methanococcus, Methanobacterium Methanobrevibacter, Methanothermobacter and/or of Methanopyrale. The bacteria can comprise acetate-decomposing methanogens as well as hydrogen-oxidising methanogens. Acetate-decomposing methanogens form methane, for example from compounds containing methyl groups, for example acetic acid, by way of them splitting off the methyl group and reducing it into methane. Hydrogen-oxidising methanogens however reduce carbon dioxide with hydrogen into methane and water as well as by converting formic acid (HCOOH). The first reactor is preferably closed off in an airtight manner, so that an anaerobic fermentation can be ensured.

The first residence time is a time in which the substrate remains in the first reactor. The substrate can remain in the first reactor in one go (continuously) for this time, or the first residence time can also be understood as an additive time which describes that time which a part-quantity of the substrate spends in the first reactor between a point in time of bringing the part-quantity of the substrate into the biogas facility for the first time and a point in time of letting the part-quantity of the substrate out of the biogas facility. Herein, the preferred residence time is at least 20 days, preferably at least 25 days and/or at the most 40 days, preferably at the most 35 days. The cellulose-containing and/or lignocellulose-containing substrate is typically straw, preferably rice straw. However, mixed ratios of cellulose-containing and/or lignocellulose-containing substrates and easily fermentable substances, such as for example manure (liquid manure, slurry), compost or food waste, can also be used. Herein, a mass ratio of cellulose-containing and/or lignocellulose-containing substrates $M_{C/LC}$ to a mass ratio of easily fermentable substrates $m_{fv}$ can be at least $m_{C/LC}/m_{fv}=50/1$, preferably at least $m_{C/CL}/m_{fv}=40/1$, particularly preferably $m_{C/LC}/m_{fv}=20/1$ in weight shares.

A further method step is a transferring of a part of the at least partly fermented substrate out of the first reactor into a second, heatable reactor with hyperthermophilic bacteria, wherein the hyperthermophilic bacteria are suitable for breaking down the at least partly fermented substrate. Hyperthermophilic bacteria have growth optima at temperatures of more than 60° C. Herein, the hyperthermophilic bacteria are preferably bacteria from the group of chlostridia, preferably *Chlostridium aceticum, Chlostridium thermocellum* and/or *Chlostridum stecorarium*. These can break down lignocellulose at least partly in symbiosis with other species and metabolise it into lower organic acids and short-chained alcohols. These intermediate products can be: acetic acid, formic acid, propionic acid, butyric acid, ethanol, butanol and/or butanediol. These intermediate products can subsequently be broken down further by acetogenic bacteria into hydrogen, carbon dioxide and chiefly acetic acid. Herein, the second reactor can be sealed off in an airtight manner so that an anaerobic fermentation under the exclusion of oxygen can take place.

The at least partly fermented substrate is incubated for a second residence time at a temperature in the region of at least 55° C., preferably at least 60° C., particularly preferably at least 65° C. and/or at the most 80° C., preferably at the most 75° C., particularly preferably at the most 70° C. Acetic acid is herein at least partly formed. The second residence time of the substrate in the second reactor is typically at least 10 hours, preferably at least one day and/or at the most 5 days, preferably at least two days and/or at the most three days. The formation of accompanying substances (phenols, cresols, dimethyl phenols, vanillin) can therefore be largely suppressed. Furthermore, iron compounds can be admixed to the second reactor. The iron compounds can already be brought into the substrate on introduction into the first reactor and/or directly into the thermophilic reactor. Given high concentrations, a reaction product can be brought out of the thermophilic reactor. Small quantities/residues can be removed from the system with the solid fermentation residues during the separation process. The second residence time can also be absolute or additive, as with the first residence time. The substrate can therefore remain in the second reactor for a second residence time in one go (continuously), or a sum of individual time durations which the substrate spends in the second reactor corresponds to the second residence time.

The substrate with the formed acetic acid is transferred from the second reactor back into the first reactor. Lignocellulose or cellulose which is contained in the substrate has been broken down at least in part into for example acetic acid after the incubation in the second reactor. Lignocellulose which has not been converted into acetic acid in the second incubation time was at least partly broken down into lower structures by microorganisms. The returned sludge with the formed acetic acid is incubated in the first reactor, and in particular the acetic acid is converted into methane by the mesophilic bacteria, as described above.

In a further step, methane-containing biogas is isolated from the first reactor. Herein, the biogas typically comprises 40% to 60% methane ($CH_4$), 40% to 60% of carbon dioxide ($CO_2$), 100 to 5000 ppm hydrogen sulphide ($H_2S$) and trace gases.

The method further has the advantage that biogas can be produced even with a low concentration of ammonium nitrogen. Whereas minimal ammonium nitrogen concentrations of 1.1-2.5 g NH4-N/l are assumed with known biogas facilities, the method which is described above can already produce biogas with concentrations of at least 100 mg NH4-N/l, preferably at least 150 mg NH4-N/l, particularly preferably at least 200 mg NH4-N/l and/or at the most 1 g NH4-N/l, preferably at the most 700 mg NH4-N/l, particularly preferably at the most 400 mg NH4-N/l. Furthermore, due to the adaptation of the microorganism to the low N-load, it is furthermore not essential to artificially maintain the N-concentration, for example by way of the excess load of manure or even the addition of chemical nitrogen products. Here of course, one should take into account the ratio of carbon to nitrogen. Accordingly, the invention can also be installed in fields with regard to which only small quantities of manure occur. This to some extent is an essential constituent with conventional biogas facilities.

The specific biogas formation rate of the described biogas facility or of the described method, from rice straw, can be at least 200 $Nm^3$ of methane/(t oDM), preferably at least 210 $Nm^3$ of methane/(t oDM) and/or up to 250 $Nm^3$ of methane/(t oDM), preferably up to 330 $Nm^3$/(t oDM). Herein, the residence time is typically at the most 30 days, whereas with conventional biogas facilities, given a comparatively long residence time of 180 days, comparatively low yields of only 210 $Nm^3$ of methane/(t oDM) have been achieved.

A substrate receiving volume ratio, i.e. a ratio between the volume of substrate which a reactor can receive, between the second and the first reactor is typically about $V_2/V_1=1/20$, preferably about $V_2/V_1=1/6$, particularly preferably about $V_2/V_1=1/15$. The first reactor can therefore receive for example 1000 $m^3$ of substrate, whereas the second reactor can receive 50 $m^3$ of substrate, particularly preferably 100 $m^3$ of substrate. An advantageous ratio of $V_2$ to $V_1$ can be specified by 1/6 to max. 1/20.

A volumetric load describes a quantity of organic dry matter (oDM) measured by reactor volume over a time measured in days. The volumetric load in the first reactor is typically at least 2.5 (kg oDM)/($m^3$ d), preferably at least 3 (kg oDM)/($m^3$ d), particularly preferably 3.5 (kg oDM)/($m^3$ d) and/or at the most 5.0 (kg oDM)/($m^3$ d), preferably max. 4.5 (kg oDM)/($m^3$ d).

The volumetric load of the second reactor in some embodiment examples is 5 to 20 times as high, preferably 7 to 13 time as high, particularly preferably 9 to 11 times as high as the volumetric load in the first reactor.

A solid matter feed in the form of straw, in particular rice straw, into the reactor is preferably at least 10% by weight in the feed stream, particularly preferably between 20% by weight and 40% by weight, at the most up to 70% by weight. Added to this are preferably 30 to 90% by weight of manure, for example bovine manure, particularly preferably 60% by weight. Recirculate can be added for the processing of liquid as an alternative to slurries and/or water, preferably 5 to 8% by weight, particularly preferably 10 to 70% by weight. In total, the aforementioned solid matters can preferably add up to 100%.

The substrate can be intermixed, in particularly continuously intermixed in the first and/or second reactor by way of a pump device and/or stirring device. This can be advantageous in order to prevent sediments and a sticking of the substrate, so that an as uniform as possible temperature and nutrient distribution can be generated.

Furthermore, the method can be carried out at least partly in a circulating manner, i.e. the steps "transferring a part of the at least partly fermented substrate out of the first reactor into a second, heatable reactor with hyperthermophilic bacteria, wherein the hyperthermophilic bacteria are suitable for breaking down the at least partly fermented substrate" and "returning the substrate with acetic acid out of the second reactor into the first reactor" can be repeated. A circulation of substrate can therefore be generated and the substrate can be further broken down with each renewed run-through of a reactor. The reactions in the reactor can influence one another, since for example the reaction product is in the second reactor (acetic acid) and a reactant is in the first reactor. A methane production in the first reactor is therefore directly responsible for a methane production, but a cellulose or lignocellulose decomposition is indirectly necessary in the second reactor. An advantageous, further decomposition, in particular of difficultly fermentable substrate such as for example lignocellulose can therefore generate an increased methane production compared to a single run of substrate through the first and/or second reactor.

Fermentation residues which remain in the first reactor and which are essentially not broken down by the bacteria any further after a fermentation in the first reactor can be led out of the first reactor and drained. One can determine for example when a biogas yield drops via a measuring device which measures how high the biogas yield is at a momentary point in time. If biogas is no longer produced to an adequate degree or only a small amount continues to be produced, then substrate residues which remain in the reactor for the most part are no longer further broken down. These substrate residues are accordingly fermentation residues. A point in time at which the fermentation residues are to be discharged can also be fixed and not determined by a biogas yield. For example, fermentation residues can be discharged regularly after a first residence time. An accordingly separated process fluid can be at least partly fed again to the first reactor via a discharge conduit. Herein, fermentation residues are liquid or solid residues which remain after substrate has been fermented. On draining, liquids can be separated from the solid fermentation residues in a manner such that a solid fermentation residue and a process liquid arise. Solid fermentation residues can be brought out of the biogas facility and the process fluid can be fed to a mixing device or directly to the first reactor. The discharge conduit can therefore lead into a drainage device and from there either into the first reactor or into the mixing device. Substrate which is to be fed to the first reactor can be mixed with the process fluid in the mixing device in order to achieve a more homogeneous substrate consistency and/or to be able to adjust a dry matter content. Herein, the dry matter is that share of a substance which remains after the complete removal of water. A substrate and process liquid mixture can be led out of the mixing device into the first reactor.

Any undesirable substances can be brought out of the second reactor. Silicic acid can occur for example as an undesirable product on breaking down the biomass. This can get into the first reactor via circulation devices and act in a manner in which it inhibits the formation of methane. In order to reduce a concentration of silicic aid which inhibits methane formation and/or of other substances which are harmful to bacteria, these substances can therefore preferably be brought out when already in the second reactor. This can therefore favour the formation of methane and have a positive effect on the efficiency of the biogas facility.

Furthermore, as already mentioned, the cellulose-containing substrate can comprise lignocellulose. Herein, straw-like biomass, for example straw, in particular wheat straw, hay, and/or rice straw and/or their silage can preferably be used as a substrate. Rice straw is particularly suitable, since a high energy content is present here due to a high share of lignocellulose. This energy can be rendered useable in the form of biogas in the first reactor by way of a decomposition of the lignocellulose in the second reactor. Herein, substrates are conserved by lactic acid bacteria by way of silaging, wherein lactic acid bacteria have converted the sugar which is contained in the substrate into acids. Furthermore, the biogas facility can also be fed with manure or manure-like residues, preferably with chicken manure, pig manure or bovine manure.

A pH-value of the substrate in the first reactor typically lies in the pH-neutral to slightly alkaline range, so that mesophilic bacteria can live under as favourable living conditions as possible, in order to encourage a formation of methane. Favourable living conditions typically lie between pH 6.6 and 8.3.

A pH-value in the second reactor is typically 3.5, preferably at least 4.5 and/or at the most 7.5; preferably at the most 6.5. Such a pH-value can encourage a formation of acetic acid in the second reactor by the hyperthermophilic bacteria. In turn, methane can be formed from acetic acid in the first reactor, so that a higher acetic acid production indirectly encourages a methane formation.

Typically, substrate fibres can be reduced in size before bringing the substrate into the first reactor. The substrate fibres can be mechanically pre-treated for example by way of a cutting mill. Herein, rice straw is typically cut up into a fibre length of 40 mm, wherein of course other fibre lengths, preferably shorter than 60 mm, are conceivable for rice straw as well as for other substrate fibres. Such a size reduction can have the advantage that substrate fibres cannot wrap themselves around the stirring devices or rotors of pumps and thereby compromise their functioning.

The substrate, in particular straw, manure, and supernatant liquid can be blended before being brought into the first reactor. However, the straw, in particular rice straw, can also be brought into the first reactor without any previous admixing of manure, process fluids and/or other biomass. This has the advantage that an intrinsic heating by way of dissolved oxygen in the mixture due to respiration processes and a formation of methane after a certain dwell time and energy losses which result therefrom can be prevented. Moreover, the supply container is often not able to be cooled, so that no inactivation of microorganisms can take place due to this. The rice straw is preferably essentially dried, mechanically reduced in size, and a loose aggregate material. The rice straw can be brought into the first reactor by way of for example a screw feeder. Other biomasses (for example slurries and/or silages) can be brought into the first reactor parallel to this, for example by way of pumps. The invention further relates to a biogas facility for producing biogas, comprising a first reactor, a second reactor and a circulation device. Herein, the first reactor comprises mesophilic bacteria which are suitable for producing methane from acetic acid, hydrogen and carbon dioxide. The second reactor is heatable and comprises hypothermic bacteria which are suitable for the at least partial anaerobic fermentation of a cellulose-containing, preferably lignocellulose-containing substrate, into acetic acid. The circulation device for producing a biomass circulation between the first reactor and the second reactor comprises a conveying device and at least one connection conduit which connects the first reactor and the second reactor. The conveying device is configured for conveying substrate through the connection conduit from the first reactor into the second reactor as well as from the second reactor into the first reactor. Herein, the circulation device can comprise a pump device which pumps substrate from one reactor into the other. Herein, the pump device can comprise for example an eccentric screw pump.

The connection conduit for transporting or delivering substrate from the first into the second reactor can comprise an aeration device. This can be advantageous, as anaerobic bacteria strains of the first reactor are at least partly killed or inactivated. In some embodiment examples, a valve, preferably a one-way valve, and a pump are provided in the connection conduit upstream and downstream of the aeration device. Given, for example, a closed valve downstream of the aeration device, substrate can thus be pumped by this pump out of the first reactor through a valve which is opened upstream of the aeration device, into the aeration device and be aerated there. The aeration device can optionally be situated at a higher level compared to the exit of the connection conduit out of the first reactor, so that the pump pumps the substrate upwards (i.e. in a direction which is opposite to the weight force) in a manner such that the substrate is subjected to a pressure due to the Bernoulli's equation. This can be realised for example by way of pumping the substrate into an aeration device in the form of a vertical column. The valve upstream of the aeration device is closed subsequently to the aeration or after the aeration device is filled. The valve downstream of the aeration device is opened after the aerating. In those embodiments, in which the substrate is subjected to a pressure, the substrate flows into the second reactor due to the pressure difference and the tendency of the substrate to create a pressure compensation given an opened second valve. Other embodiments can also envisage pumping the substrate out of the aeration device into the second reactor by way of a further pump.

In some embodiments, the second reactor can comprise a further feed conduit. For example, easily fermentable substances can be led directly into the second reactor via this feed conduit, in order to optimise the fermentation process which takes place there and/or to regulate a ratio of difficultly fermentable substances to easily fermentable substances. A pH-value regulation into the acidic range can therefore be encouraged. An addition of chemicals is therefore typically unnecessary.

The biogas facility can further comprise a drainage device for separating a process fluid on draining fermentation residues. Herein, the first reactor can be connected to the drainage device via a discharge conduit, for leading away the fermentation residues. The discharge conduit can be designed for example as a pipe conduit or as a hose. A pumping-away of fermentation residues into an additional container is likewise conceivable.

The fermentation residues are those substrate residues which after fermentation in the first reactor and/or second reactor are essentially no longer further broken down by the mesophilic and/or hyperthermophilic bacteria.

The biogas facility can comprise a mixing device which is arranged upstream of the first reactor and is connected to this first reactor by way of a feed conduit. Substrate can hence be mixed with a process fluid in a manner such that a dry matter content of the substrate which is feedable through the feed conduit to the first reactor can be adjusted. Herein, a dry matter content is typically at least 8%, preferably at least 12% and/or at the most 30%, preferably at the most 20%.

The biogas facility can further comprise a return device for returning the process fluid into the first reactor. The process fluid can be led into the mixing device and/or into the first reactor and can therefore be mixed with substrate which is to be fermented. Herein, the process fluid can make sense inasmuch as it liquefies and homogenises substrates which are difficult to ferment, so that the bacteria has better access to the substrate and fermentation is assisted.

In some embodiments, the connection conduit between the first reactor and the second reactor comprises a two-way valve arrangement and/or aeration device. Additionally, or alternatively, the circulation device can also comprise two connection conduits between the first reactor and the second reactor. A circulation of substrate between the first and the second reactor can therefore be generated. The substrate which cannot or is only difficult to be metabolised into methane by the mesophilic bacteria is broken down further in the second reactor. Herein, it is particularly lignocellulose-containing substrate which is broken down further in the second reactor. After a decomposition of the preferably lignocellulose-containing substrate, this can be led through the connection conduits back into the first reactor, in order to at least partly ferment into methane there. This cycle can be repeated as often as desired.

The circulation device can comprise a pump, for example an eccentric screw pump, for delivery the substrate. Of course, any other pump systems which are suitable for the transport of at least viscous biomass, such as rotary pumps are also conceivable. The use of peristaltic pumps is particularly suitable for handling rice straw sludge.

The biogas facility can typically comprise at least one stirring device and/or pump device for intermixing the substrate in the first reactor and/or second reactor. The stirring device can be stirrers, for example central stirrers, submersible motor stirrers and/or paddle stirrers. Other stirrers can of course also be used. Herein, the flow characteristics of the substrate or of the biomass can advantageously be improved, an essentially constant composition of the biomass ensured and herewith a fermentation process improved.

The first reactor can be heatable in a manner such that a temperature of at least 30° C., preferably at least 35° C., particularly preferably at least 40° C. can be set. The second reactor can be heatable in a manner such that a temperature of at least 55° C., preferably at least 60° C., particularly preferably at least 65° C. can be set.

In a further embodiment, the biogas facility can comprise a pre-treatment device for the size reduction of the substrate fibres. Therein, the substrate fibres can be cut to an adjustable fibre length, preferably max 40 mm, so that an essential homogeneous intermixing of the substrate can be achieved by the pump or stirrer and a wrapping of substrate fibres around stirrer blades or a blockage of pipe conduits or pumps by way of adhesions or knotted substrate fibres can be counteracted.

The second reactor preferably comprises bacteria selected from the group *Clostridium* spp., preferably *Clostridium aceticum*, *Clostridium thermocellum* and/or *Clostridium stecorarium* and/or Thermotogaceae.

In some embodiment examples, the inoculation of the hyperthermophilic reactor is effected before the first feeding with substrates. An inoculation culture can be taken for example from existing hyperthermophilic reactors according to the described patent claim (so-called activated sludge). Furthermore, a propagation of hyperthermophilic microorganisms by way of the addition of animal residual substances and/or biomasses from anaerobic/aerobic decomposition process (rotting, composting, respiration processes) is possible in the second reactor.

The described biogas facility can be used for carrying out the described method. The features which are described with regard to the method can accordingly apply to the biogas facility and the features which are described with regard to the biogas facility can further apply to the method.

In existing biological treatment systems, one cannot rule out easily fermentable substances (hexoses, starches) being metabolised by respiratory (aerobic) processes into carbon dioxide. A formation of high-energy methane could fail to materialise due to these substances. This is avoided in the described method, since fresh masses are first broken down/fermented in an anaerobic manner. Aerobic respiratory processes do not take place. It is only the substances which are difficult to break down (preferably celluloses, hemicelluloses, lignocelluloses and/or waxes) which are available to the specific microorganisms for forming organic acids and alcohols. The heat quantity feed is the same when compared to existing systems. An increased energy feed does not take place.

Figure 2A:
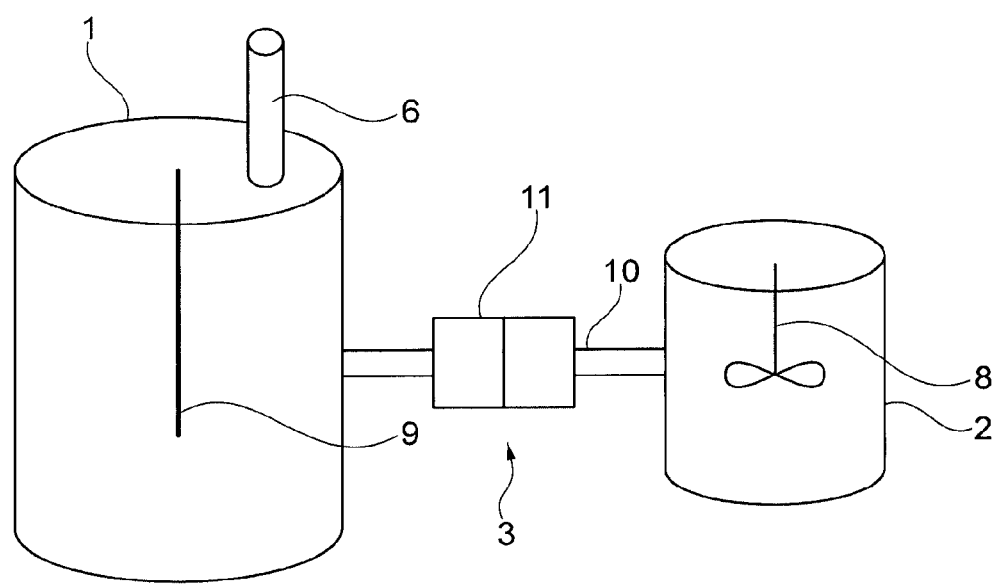
Figure 1B:
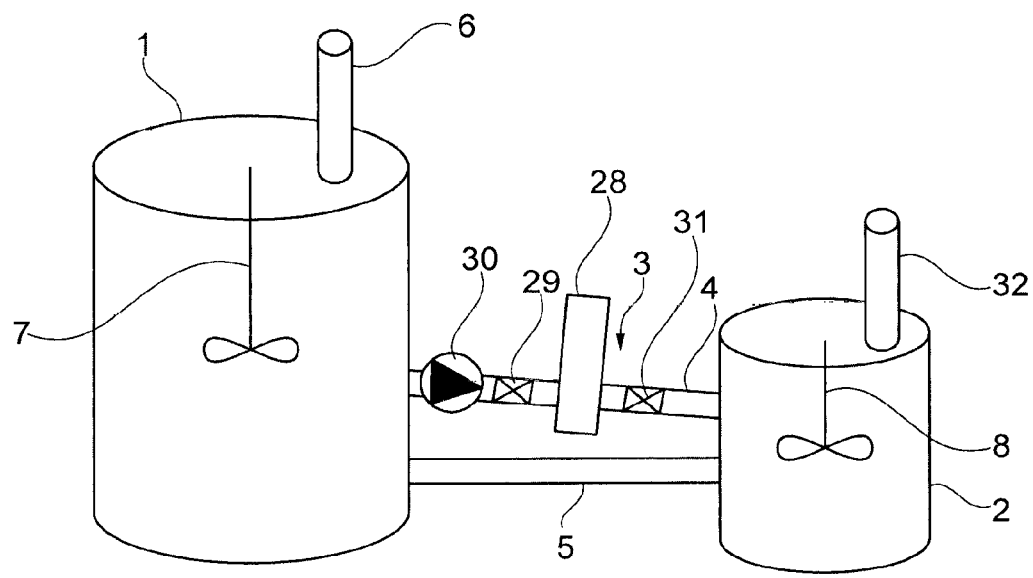
Figure 2B:
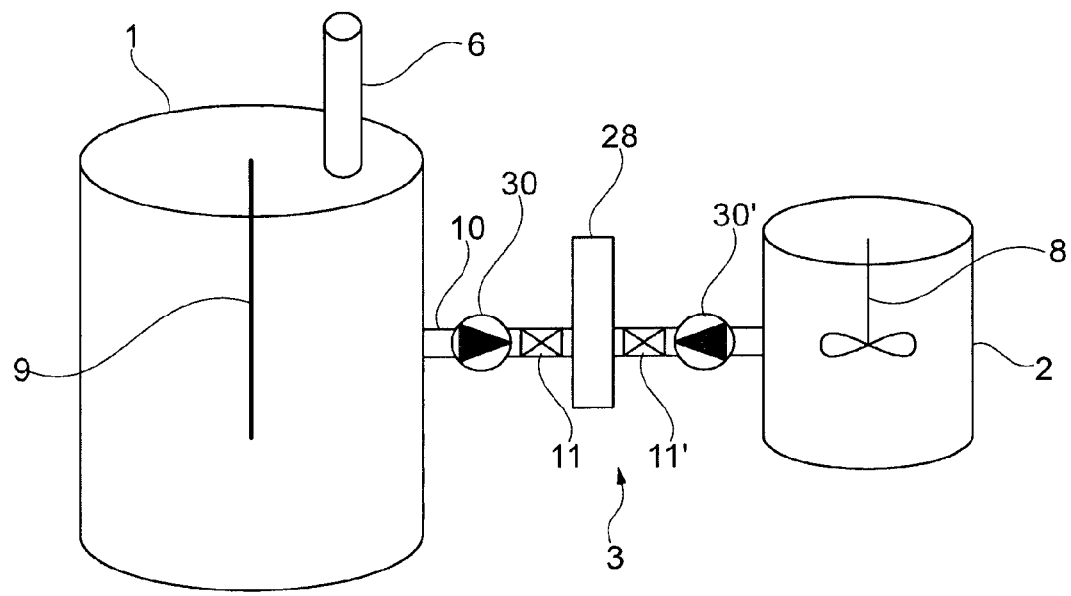
Figure 3:
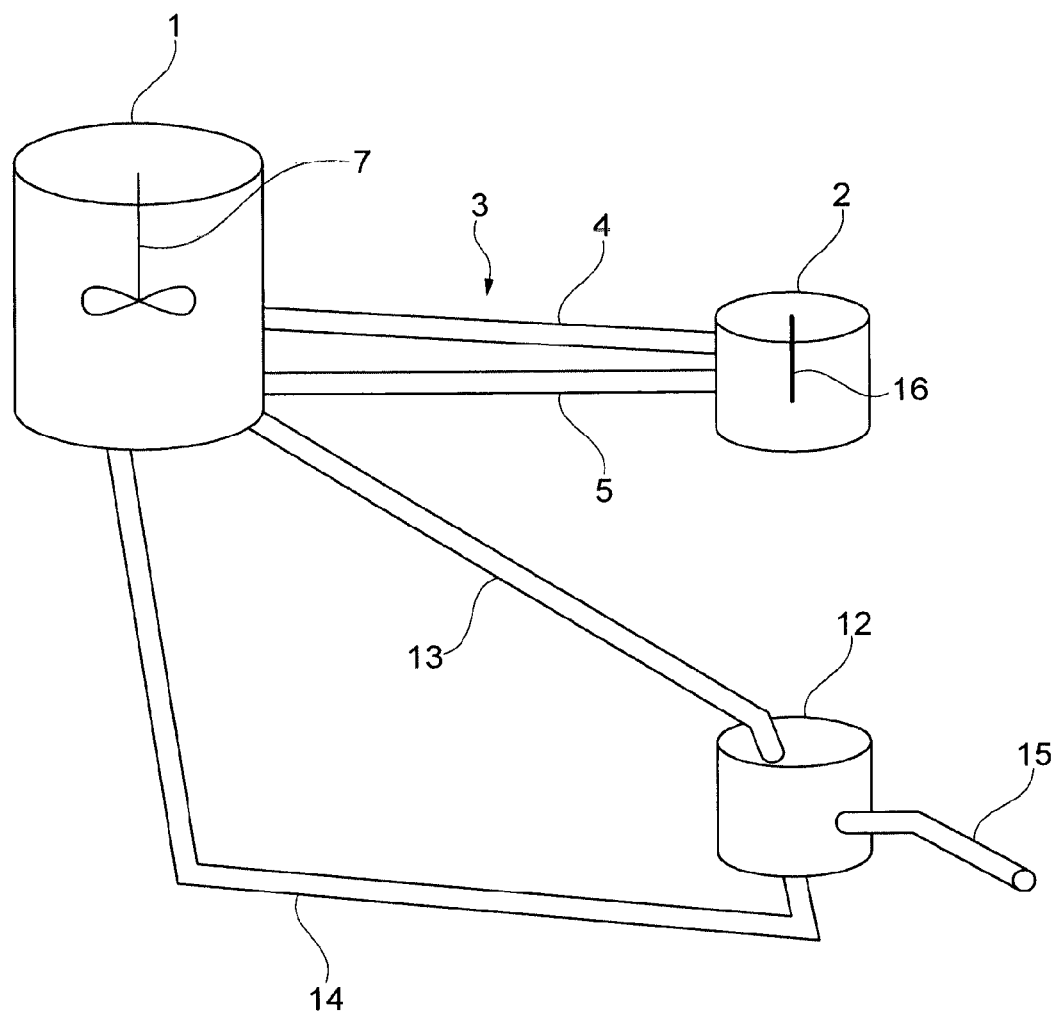
Figure 4:
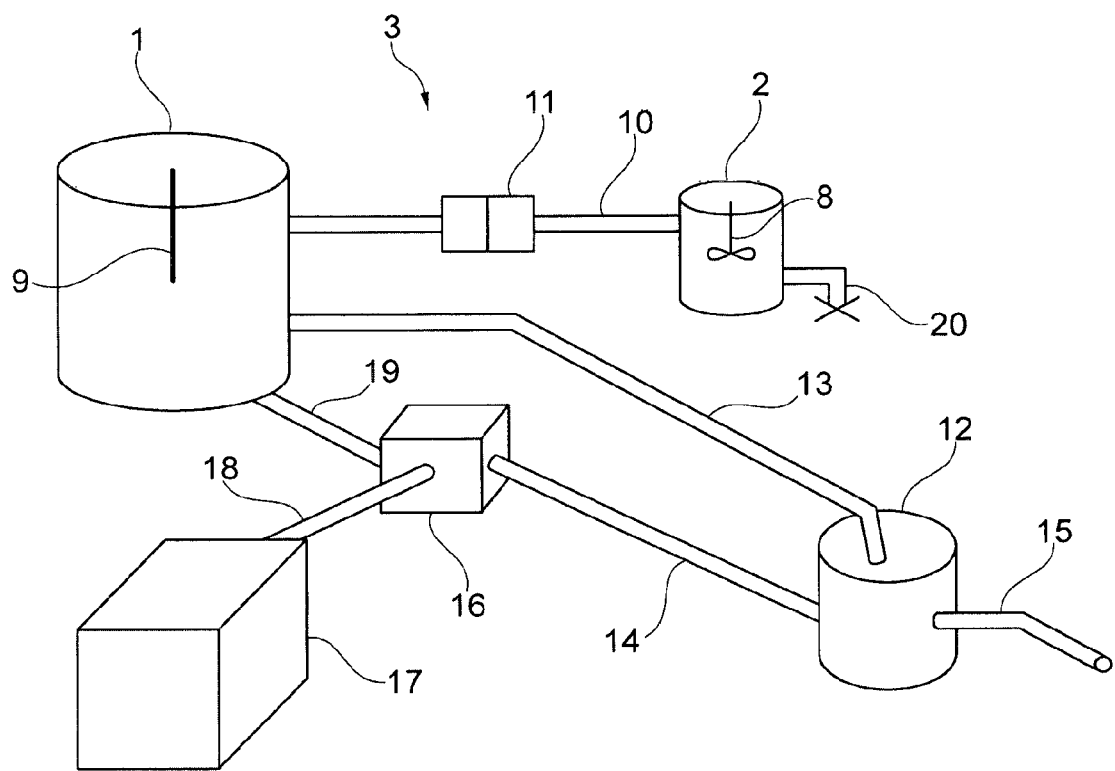
Figure 5:
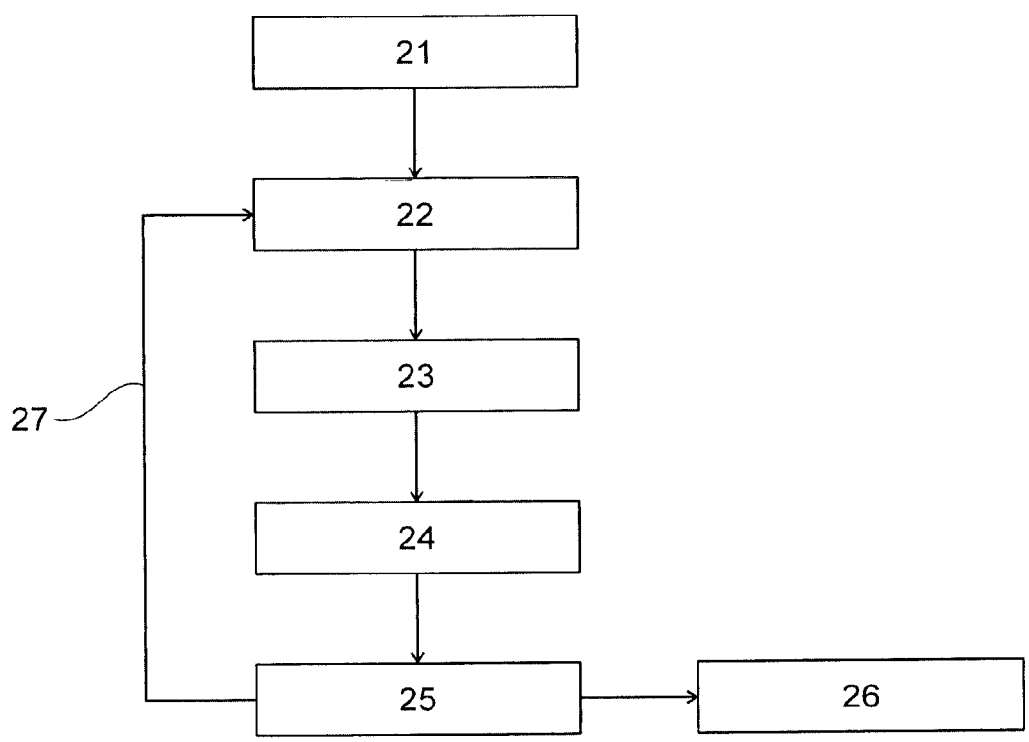

Embodiment examples of the present invention are hereinafter explained with reference to the accompanying drawings. There are shown in:

FIG. 1a: a schematic representation of a biogas facility,
FIG. 1b: a schematic representation of the biogas facility with an aeration device, FIG. 2a: a schematic representation of a biogas facility with a 2-way valve arrangement, FIG. 2b: a schematic representation of a biogas facility with a 2-way valve arrangement and an aeration device;

FIG. 3: a schematic representation of a biogas facility with a drainage device,

FIG. 4: a schematic representation of a biogas facility with a mixing device, a size-reduction device and with a drainage device, and FIG. 5: a schematic representation of a method for producing biogas.

FIG. 1a shows a biogas facility with a first reactor 1 and with a second reactor 2. A content of the first reactor 1 contains mesophilic bacteria and a cellulose-containing and lignocellulose-containing substrate, wherein the cellulose-containing and lignocellulose-containing substrate comprises rice straw, rice straw silage and chicken manure. In the shown example, the first reactor 1 is heatable and the contents of the first reactor 1 have been heated to a temperature of 33° C. However, it is also conceivable for the first reactor 1 not to be heatable and for a temperature between 20° C. and 40° C. to set in due to an exothermic fermentation process by the contained mesophilic bacteria. The mesophilic bacteria—in the present example these are archaea, and specifically Methanobacteriales, Methanococcales, Methanomicrobiales, Methanocellales—are suitable for producing methane from acetic acid. The substrate which is contained in the first reactor 1 resides for example 30 days in the first reactor 1 and at least partly ferments, so that methane is generated. A part of the at least partially fermented substrate is led out of the first reactor 1 into the second reactor 2 by way of a circulation device 3. The circulation device herein comprises a first 4 and a second connection conduit 5, wherein the at least partly fermented substrate is transported via the first connection conduit 4 from the first reactor 1 into the second reactor 2 by way of a pump device, preferably an eccentric screw pump. The second reactor 2 is heatable and the contents of the second reactor 2 are heated to a temperature of 68° C. Hyperthermophilic bacteria, for example clostridia, preferably *Clostridium aceticum, Clostridium thermocellum* and/or *Clostridium stecorarium* are in the second reactor 2. The hyperthermophilic bacteria are suitable for further breaking down the at least partly fermented substrate, in particular lignocellulose. For this, the at least partly fermented substrate remains in the second reactor for a residence time of at the most 3 days. There, the lignocellulose is converted at least partly into acetate, butanol and further acids/alcohols by the hyperthermophilic bacteria. The substrate with acetic acid is led back from the second reactor 2 into the first reactor 1 via the second connection conduit 5 by way of an eccentric screw pump. The substrate with the acetic acid is incubated in the first reactor 1 by the mesophilic bacteria and methane-containing biogas with at least 50% methane, 30% carbon dioxide, 1000 ppm hydrogen sulphide and trace gases arises. The biogas is at least partly isolated and transferred out of the first reactor 1 via a discharge device 6, i.e. a gas conduit. The remaining, at least partly fermented substrate is again transferred into the second reactor 2 via the first connection conduit 4 and there is further broken down, in order after a further residence time of 5 days in the second reactor 2 to be led again into the first reactor 1 via the second connection conduit 5 and to be incubated there again. The substrate is therefore fermented and further broken down in the first 1 as well as in the second reactor 2. This substrate circulation is repeated so often until almost no or only little biogas can be obtained from the substrate.

On transferring the at least partly fermented substrate further from the first reactor 1 into the second reactor 2, most mesophilic bacteria die in the second reactor 2 due to the high operating temperature. The hyperthermophilic bacteria die in the first reactor, at least for the most part, when these go through the second connection conduit 5 into the first reactor 1, due to the lower temperature. The first reactor 1 as well as the second reactor 2 each comprise a stirring device 7, 8, wherein the first stirring device 7 continuously intermixes the contents of the first reactor 1 and the second stirring device 8 the contents of the second reactor 2 in order to prevent deposits and adhesions of the contents and to keep the substrate in a homogeneous as possible state. In the first reactor, the substrate in weight parts is twenty times larger than the substrate in the second reactor 2.

FIG. 1b shows a biogas facility which corresponds essentially to FIG. 1a, but comprises an aeration device 28 in the connection conduit 4. A one-way valve 29 and a pump 30 are arranged upstream of the aeration device 28. A further one-way valve 30' is arranged downstream of the aeration device. The pump 30 pumps the substrate out of the first reactor 1 into the aeration device given an opened valve 29 and a closed valve 31. The valve 29 is then closed. The substrate is aerated in the aeration device. Herein, the predominantly anaerobic bacteria from the first reactor 1 which are located in the substrate which is to be aerated are inactivated or killed by the aeration. The valve 31 is subsequently opened and the aerated substrate is led into the second reactor 2. One therefore succeeds largely preventing a methane-forming fermentation from taking place in the second reactor 2. No aeration is necessary for the substrate in the return conduit from the second reactor 2 into the first reactor 1 since the bacteria of the reactor 2, predominantly clostridia, are inactivated or die due to the temperature difference in the second reactor 2 and the first reactor 1, since these bacteria require higher temperatures, corresponding to the temperatures in the reactor 2, for survival and/or for actively metabolising.

The second reactor of FIG. 1b further comprises a feed conduit 32. Easily fermentable substances can be admixed to the reactor contents by way of this feed conduit 32.

FIG. 2a shows a further embodiment example of the biogas facility of FIG. 1, wherein a pump device 9 for intermixing the substrate is used in the first reactor. The contents of the second reactor 2 are thoroughly stirred with a stirring device 8. A combination of stirring device 8 and/or pumping device 9 in the first 1 and/or the second reactor 2 is therefore likewise conceivable for a biogas facility. In particular, this can be advantageous in order to be able select a mixing device which is as inexpensive and energy-saving as possible in accordance with the size of the reactors, in order to reduce the manufacturing and operating costs of the biogas facility.

FIG. 2b shows a biogas facility which corresponds essentially to the biogas facility of FIG. 2a, but comprises a connection conduit 10 which is additionally provided with an aeration device 28, two pumps 30 and two two-way valves 11. The substrate can be pumped from the first into the second reactor 2 and vice versa by way of a respective opening and closing of the valves 11. The substrate is preferably aerated on pumping from the first reactor 1 into the second reactor 2. For this, the two-way valve 11 (analogously to the one-way valve in FIG. 1b) downstream of the aeration device is first closed and the substrate is pumped from the first reactor 1 into the aeration device 28. The two-way valve 11 upstream of the aeration device 28 is then closed and the substrate is aerated in the aeration device 28.

The two-way valve 11' downstream of the aeration device is opened after the aeration process, so that the substrate is led into the second reactor 2. The two-way valves 11 and 11' can be opened in a manner such that the substrate can only flow in the direction of the first reactor 1, for returning the substrate from the second reactor 2 into the first reactor, in order to permit a circulation. A further pump 30' is provided for this, said further pump pumping the substrate out of the second reactor 2 into the first reactor 1. Furthermore, a further valve which is closed given a return can be provided on the aeration device 28, so that the substrate is not possibly unnecessarily aerated again on being led back into the first reactor. Such a valve is not represented in FIG. 2b but can be optionally added.

The contents of the first reactor have a pH-value of 7. The contents of the second reactor 2 have a pH-value of 5.5. These pH-values correspond to the preferred pH-values of the bacteria which are brought into the first and the second reactor 1, 2.

In FIG. 2, the first reactor 1 has a volume which is twenty times larger than the volume of the second reactor 2. The two reactors 1, 2 in FIGS. 2a and 2b are connected to a circulation device 3, wherein the circulation device comprises a transport or delivery device in the form of an eccentric screw pump and a connection conduit 10 with a two-way valve arrangement 11. A through-flow direction of the substrate can be set via the two-way valve arrangement 11, so that a substrate flow from the first reactor 1 into the second reactor 2, as well as a substrate flow from the second reactor 2 into the first reactor 1 can run through the connection conduit 10. As has already been described and shown in FIGS. 1a and 1b, biogas can be isolated and led out via the discharge device 6. A circulation of substrate can of course also be generated by way of transferring substrate out of the one reactor, for example reactor 1, into an intermediate container and from the intermediate container into the other, for example the second reactor 2. This can be advantageous for example if the first reactor and the second reactor with regard to location are to be installed remotely from one another and long, connection conduits with complex paths would be necessary.

Furthermore, the residence time can be effectively related to the reactor volumes. The first reactor has a volume which is twenty times larger than the volume in the second reactor. Only a part-quantity of the substrate in the first reactor can therefore fit into the second reactor, in this example a twentieth. Since the entire contents of the first reactor is to run through the second reactor and is to incubate in the second reactor for 2.5 days at a time, a first residence time in the first reactor of 50 days results. The substrate for example as fermentation residue is then led out of the first reactor after 50 days.

FIG. 3 shows a biogas facility with a drainage device 12 which is connected to the first reactor 1 via a discharge conduit 13. Fermentation residues which arise after fermentation in the first reactor 1 and/or the second reactor 2 are then led via the discharge conduit 13 into the drainage device 12. This can be effected for example at a point in time when a biogas production drops and a volume flow in the discharge device 6 drops below a measured limit value, for example on dropping 5-10% below the value of the previous volume flow of biogas [$Nm^3/h$]. Of course, the fermentation residues can also be discharged out of the first reactor into the drainage device after a first residence time, here for example after 50 days. There, a process fluid is separated from the fermentation residues. This process fluid is led at least partly into the first reactor via a return device 14 and is mixed there with the substrate by way of the stirring device 7. One can therefore counteract a clotting of the substrate and a ratio of a liquid content of the substrate to a dry matter content of the substrate can be adjusted. A solid fermentation residue, i.e. the drained fermentation residue can be further discharged out of the drainage device 12 via a discharge element 15, for example a tube. The at least partly fermented substrate is thoroughly mixed (intermixed) in the second reactor 2 by way of a pumping device 16, preferably in a continuous manner.

A biogas facility which corresponds to the construction of the biogas facility in FIG. 2a is represented in FIG. 4. However, it comprises further elements such as for example a drainage device 12, a mixing device 16, a pre-treatment device 17, and a silicic acid discharge device 20. Before substrate is fed to the first reactor 1, it is reduced in size in the pre-treatment device 17 to a fibre length of preferably 40 mm, preferably by way of a mechanical cutter or cutting mill. The substrate fibres, in particular rice straw and wheat straw which are reduced in size to 40 mm are led through a tube 18 into the mixing device. A drainage device 12 is provided as also in FIG. 3. This leads the separated process fluid via the return device 14 into the mixing device 16. The size-reduced substrate and process fluid are mixed in the mixing device 16 before it is led further into the first reactor 1 via a feed conduit 19. In the shown example, apart from the size-reduced substrate and the process fluid, no further substances are fed to the mixing device 16. Of course, further substance constituents, for example manure, can be led to the mixing device 16 via further conduits.

The biogas facility which is shown in FIG. 4 further comprises a silicic acid discharge device 20. This is preferably assembled onto the second reactor 2, so that silicic acid which arises partly due to clostridia on decomposition of the lignocellulose and can act in a manner inhibiting the methane formation, can be brought out before transferring the substrate further into the first reactor 1. One can therefore succeed in a methane formation not being inhibited in the first reactor by the mesophilic bacteria and the efficiency of the biogas facility can therefore be improved. The silicic acid can be separated for example by a silicate filter and silicic acid filter or also be separated out of the liquid phase by way of prior precipitation reactions, and subsequently discharged from the second reactor 2.

FIG. 5 schematically describes an exemplary sequence of the method for producing biogas with the described biogas facility. In a first step 21, first a cellulose-containing substrate, containing rice straw and bovine manure is at least partly fermented in a first reactor at a temperature of 30 to 48° C. for a first residence time of 30 days. Mesophilic bacteria which can metabolise the substrate are contained in the first reactor.

In a second step 22, the at least partially fermented substrate is led out of the first reactor into a second reactor. The second reactor is heated and its contents have a temperature of 68° C. Hyperthermophilic bacteria, which are suitable for breaking down the at least partly fermented substrate, in particular the lignocellulose, are in the second reactor.

In a third step 23, the hyperthermophils incubate the at least partly fermented substrate in the second reactor during a residence time of preferably 2 days. The hyperthermophilic bacteria, in particular bacteria of the genus *Clostridia*, herein break down the partially decomposed substrate, in particular cellulose and lignocellulose and herein preferably produce acetic acid, apart from other organic acids.

The at least partially decomposed substrate is then led out of the second reactor into the first reactor in a fourth step 24.

In a fifth step 25, the led-back substrate is incubated again by the mesophilic bacteria in the first reactor. Herein, methane-containing biogas arises at least in part, and this is isolated and led out of the first reactor in a sixth step 26.

Remaining, at least partially decomposed substrate is led further back into the second reactor and the described steps 22, 23, 24, 25 and 26 repeated, so that a loop 27 is created. Steps 22 to 26 are repeated until almost no more methane-containing biogas can be extracted, for example after a threefold repetition. Fermentation residues can thereafter be discharged, the biogas facility fed afresh with substrate and the method carried out once again.

Of course the steps—in particular an incubation in the first and second reactor, i.e. the steps 21, 23 and 25—in part can also take their course at the same time. Furthermore, it is also conceivable for a circulation of substrate to take place, the substrate to be incubated and the methane to be discharged, in a continuous manner. All steps 21 to 26 can therefore also take their course in time intervals (so-called fed batch method).

A typical substrate composition in the first reactor and in the second reactor in the course of the method is hereinafter explained in more detail in an embodiment example. Of course, the details specified hereinafter can also differ in other embodiment examples.

A further embodiment example is explained in more detail hereinafter. A stationary operation is assumed on considering the method. At the beginning of the method, the first reactor comprises a content for example of 3000 m³ of substrate. The necessary microorganisms for the biogas process are located therein. Temperatures of 40-48° C. are ensured via a heat source. The substrate is mixed in time intervals by way of stirrers and/or mixing devices and the formed biogas is driven out of the liquid phase. A new distribution of biomass/bacteria suspension is further produced.

100 t of substrate are fed to the first reactor daily. The solid matter feed can herein be 14 t per feed. This in turn is composed of 60-65% dry mass % (DM %) of rice straw in the mixture (with 15% water content), 20-25 DM % of bovine manure, 10-20 DM % of recirculate with mesophilic bacteria. Approx. 100 t of substrate/sludge with a dry mass share of 10-12% DM % has been fed to the second reactor at the beginning of the observation time period after a first transfer. The solid matter share can be composed for example of 60-65 DM % of rice straw, 25 DM % weight percent of bovine manure. The remaining share consists of residual substances of short-circuit flows as well as of inorganic substances, ash as well as other foreign matter. Disregarding the 10 t of solid matter, the feed stream comprises up to 90 t of water.

Up to 30% of the dry mass is broken up into soluble constituents for a residence time of for example of 3 days in the second reactor. This is typically realised by the performance capability of the hyperthermophilic microorganism which can be cultivated at 55-80° C. The temperature optimum depends on the addition of the substrate and its composition. Herein, up to 10 g/l of acetic acid can accumulate during the breakdown process, and this is led back into the first reactor 1 and converted into biogas.

The invention claimed is:

1. A method for producing biogas comprising the following steps: at least partial fermenting of a cellulose-containing substrate for a first residence time at a temperature in the region of 20° C. to 55° C. in a first reactor with mesophilic bacteria suitable for producing methane from acetic acid;
transferring a part of the at least partially fermented substrate out of the first reactor into a second, heatable reactor with hyperthermophilic bacteria, wherein the hyperthermophilic bacteria is suitable for breaking down the at least partly fermented substrate;
incubating the at least partly fermented substrate at a temperature in the region of 55° C. to 80° C. for a second residence time, wherein acetic acid is formed at least partly;
returning the substrate with acetic acid out of the second reactor into the first reactor;
incubating the substrate with acetic acid in the first reactor; and
isolating methane-containing biogas out of the first reactor;
wherein the method is carried out in a biogas facility, the facility comprising:
a first reactor containing mesophilic bacteria which are suitable for methane production from acetic acid, hydrogen and carbon dioxide;
a second heatable reactor comprising hyperthermophilic bacteria which are suitable for the preferably anaerobic fermentation of cellulose-containing substrates into acetic acid; and
a circulation device for producing a biomass circulation between the first reactor and the second reactor, wherein the circulation device comprises a conveying device and at least one connection conduit which connects the first reactor and the second reactor, wherein the connection conduit comprises an aeration device, and wherein the conveying device is configured for conveying substrate through the connection conduit from the first reactor into the second reactor as well from the second reactor into the first reactor.

2. The method according to claim 1, wherein the cellulose-containing substrate has an ammonium nitrogen concentration of at least 100 mg NH4-N/l.

3. The method according to claim 1, comprising:
transferring a part of the at least party fermented substrate out of the first reactor into a second, heatable reactor; and
transferring the part of the at least partly fermented substrate out of the first reactor into an aeration device for inactivating anaerobic bacteria.

4. The method according to claim 1, comprising repeating at least once the steps of:
transferring a part of the at least partly fermented substrate out of the first reactor into a second, heatable reactor with hyperthermophilic bacteria, wherein the hyperthermophilic bacteria are suitable for breaking down the at least partly fermented substrate; and
returning the substrate with acetic acid out of the second reactor into the first reactor.

5. The method according to claim 1, wherein fermentation residues which remain in the first reactor and which after a fermentation in the first reactor are essentially not further broken down by the mesophilic bacteria are led out of the first reactor and drained, wherein an accordingly separated process liquid is at least partially fed back into the first reactor via a discharge conduit.

6. The method according to claim 1, wherein the mesophilic bacteria are selected from the group of archaea and/or
that the hyperthermophilic bacteria are selected from the group of Clostridiaceae and/or Thermotogaceae.

7. The method according to claim 1, wherein the cellulose-containing substrate comprises lignocellulose
and/or
that the lignocellulose-containing substrate comprises straw.

8. The method according to claim 1, wherein a pH-value of the substrate in the first reactor lies in the neutral to slightly alkaline range
and/or
that a pH-value of the substrate in the second reactor is at least 4.0 and/or at the most 6.5.

9. A biogas facility for producing biogas, comprising
a first reactor containing mesophilic bacteria which are suitable for methane production from acetic acid, hydrogen and carbon dioxide;
a second heatable reactor comprising hyperthermophilic bacteria which are suitable for the preferably anaerobic fermentation of cellulose-containing substrates into acetic acid; and
a circulation device for producing a biomass circulation between the first reactor and the second reactor, wherein the circulation device comprises a conveying device and at least one connection conduit which connects the first reactor and the second reactor, wherein the connection conduit comprises an aeration device, and wherein the conveying device is configured for conveying substrate through the connection conduit from the first reactor into the second reactor as well from the second reactor into the first reactor.

10. The biogas facility according to claim 9, further comprising:
a first one-way valve located upstream of the aeration device; and
a second one-way valve located downstream of the aeration device.

11. The biogas facility according to claim 9, further comprising:
a drainage device for separating a process liquid from a fermentation residue upon a drainage of the fermentation residue after a fermentation in the first reactor, wherein the first reactor is connected to the drainage device via a discharge conduit, for discharging the fermentation residues.

12. The biogas facility according to claim 9, further comprising:
a mixing device which is arranged upstream of the first reactor and is connected to the first reactor by a feed conduit, for mixing substrate with a process fluid in a manner such that a dry matter content of the substrate which is feedable through the feed conduit to the first reactor can be adjusted.

13. The biogas facility according to claim 11, further comprising:
a return device for returning the process fluid into the first reactor.

14. The biogas facility according to claim 9, wherein at least one of: the connection conduit comprises a two-way valve or the circulation device comprises two connection conduits between the first reactor and the second reactor.

15. The biogas facility according to claim 9, wherein at least one of: the circulation device comprises at least one pump for delivering substrate or the biogas facility comprises at least one of: at least one stirring device or at least one pump device for intermixing the substrate in at least one of the first reactor or the second reactor.

16. The biogas facility according to claim 9, wherein at least one of: the first reactor is heatable in a manner such that a temperature of at least 30° C. can be set or the second reactor is heatable in a manner such that a temperature of at least 65° C. can be set.

* * * * *